United States Patent

Pees et al.

Patent Number: 5,948,783
Date of Patent: Sep. 7, 1999

[54] FUNGICIDAL TRIFLUOROMETHYLALKYLAMINO-TRIAZOLOPYRIMIDINES

[75] Inventors: Klaus-Juergen Pees, Mainz; Guenter Krummel, Vendersheim; Henry Van Tuyl Cotter, Ingelheim; Guido Albert, Hackenheim; Annerose Rehnig, Ingelheim; Leslie May, Gau-Algesheim; Waldemar Pfrengle, Seibersbach, all of Germany

[73] Assignee: American Cyanamid Company, Madison, N.J.

[21] Appl. No.: 09/054,580

[22] Filed: Apr. 3, 1998

Related U.S. Application Data

[60] Provisional application No. 60/043,820, Apr. 14, 1997.
[51] Int. Cl.[6] ............... A01N 43/54; C07D 487/04
[52] U.S. Cl. ............................ 514/258; 544/263
[58] Field of Search ............... 544/263; 514/258

[56] References Cited

U.S. PATENT DOCUMENTS 5,593,996  1/1997  Pees et al. ............... 544/263

*Primary Examiner*—Phyllis G. Spivack
*Attorney, Agent, or Firm*—Joseph M. Mazzarese

[57] ABSTRACT

The novel compounds of formula I:

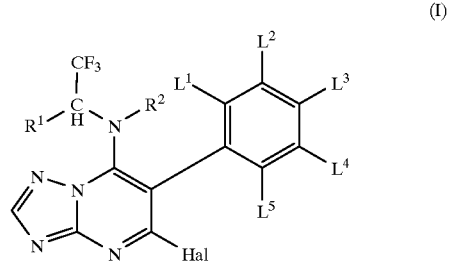

(I)

wherein $R^1$, $R^2$, Hal and $L^1$ through $L^5$, are defined in the specification show selective fungicidal activity.

8 Claims, No Drawings

FUNGICIDAL TRIFLUOROMETHYLALKYLAMINO-TRIAZOLOPYRIMIDINES

This application claims priority from copending provisional application(s) Ser. No. 60/043,820 filed on Apr. 14, 1997.

BACKGROUND OF THE INVENTION

This invention relates to certain triazolopyrimidine compounds, a process for their preparation, compositions containing such compounds, a method for combating a fungus at a locus comprising treating the locus with such compounds and their use as fungicides.

EP-A-0 071 792 claims compounds of the general formula

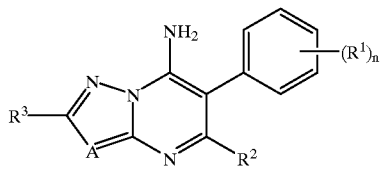

in which $R^1$ represents alkyl, halogen, alkoxy, cyano, cycloalkyl, aryl, aryloxy, arylthio, aralkyl, arylthio, arylalkyl, arylalkyloxy or arylalkylthio each optionally substituted by halogen or alkoxy; or $(R^1)_n$ represents a benzene, indane or tetrahydronaphthalene ring fused with the phenyl ring, aromatic moieties in the above groups being optionally substituted by alkyl, alkoxy, halogen or cyano; n is 1 or 2; $R^2$ and $R^3$ are each hydrogen, alkyl or aryl, A represents a nitrogen atom or a $CR^4$ group, and $R^4$ is as $R^2$ but can also be halogen, cyano or alkoxycarbonyl or together with $R^3$ can form an alkylene chain containing up to two double bonds. The compounds are said to be active against various phytopathogenic fungi, especially those of the phycomycete class. However evidence of fungicidal activity is only provided for these compounds against *Plasmopara viticola*, a member of the oomycete class of fungi. EP 0 550 11 3-A2 claims compounds of the general formula

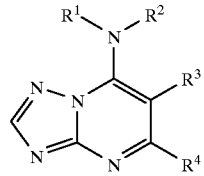

in which $R^1$ represents an optionally substituted alkyl, alkenyl, alkadienyl, cycloalkyl, bicycloalkyl or heterocyclyl group; $R^2$ represents a hydrogen atom or an alkyl group; or $R^1$ and $R^2$ together with the interjacent nitrogen atom represent an optionally substituted heterocyclic ring; $R^3$ represents an optionally substituted aryl group; and $R^4$ represents a hydrogen or halogen atom or a group —$NR^5R^6$ where $R^5$ represents a hydrogen atom or an amino, alkyl, cycloalkyl or bicycloalkyl group and $R^6$ represents a hydrogen atom or an alkyl group. Thus, compounds in which $R^1$ is a trifluoroethyl group are generally embraced by this patent application. However, there is no single compound disclosed in which $R^1$ is a trifluoromethylalkyl group.

SUMMARY OF THE INVENTION

The present invention provides a compound of formula I

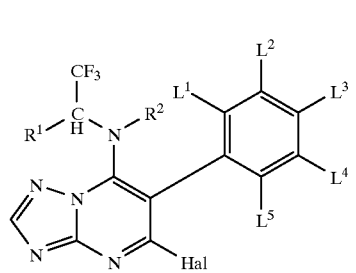

(I)

in which
$R^1$ and $R^2$ each independently represent a hydrogen atom or an optionally substituted alkyl, alkenyl, alkynyl or alkadienyl group,
Hal represents a halogen atom
$L^1$ through $L^5$ each independently represent an hydrogen or halogen atom or an alkyl group.

The new compounds show an excellent selective fungicidal activity in various crops.

It is an object of the present invention to provide novel, selective fungicidal compounds.

It is also an object of the invention to provide methods for controlling undesired fungus by contacting said plants with a fungicidally effective amount of the new compounds.

It is another object of the invention to provide selective fungicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the novel compounds of formula

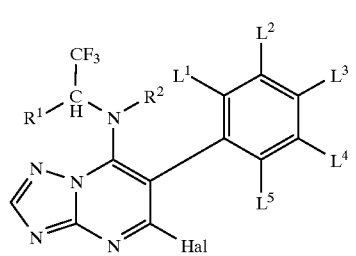

(I)

in which $R^1$, $R^2$, Hal and $L^1$ through $L^5$ have the meaning given above for formula I show an excellent fungicidal activity against a broad range of fungi.

In general terms, unless otherwise stated, as used herein the term halogen atom may denote a bromine, iodine, chlorine or fluorine atom, and is especially a bromine, chlorine or fluorine atom.

Hal represents preferably fluorine, chlorine, bromine or iodine, in particular chlorine.

Optionally substituted moieties may be unsubstituted or have from one up to the maximal possible number of substituents. Typically, 0 to 3 substituents are present.

In general terms, unless otherwise stated herein, the terms alkyl, alkenyl, alkynyl, alkadienyl as used herein with respect to a radical or moiety refer to a straight or branched chain radical or moiety. As a rule, such radicals have up to 10, in particular up to 6 carbon atoms. Suitably an alkyl moiety has from 1 to 6 carbon atoms, preferably from 1 to 3 carbon atoms. A preferred alkyl moiety is an ethyl or especially a methyl group. Suitably an alkenyl moiety has from 2 to 6 carbon atoms. A preferred alkenyl moiety is allyl or especially a 2-methylallyl group.

The invention especially relates to compounds of the general formula I in which any alkyl part of the groups $R^1$ and/or $R^2$ which may be straight chained or branched, contains up to 10 carbon atoms, preferably up to 9 carbon atoms, more preferably up to 6 carbon atoms, any alkenyl or alkynyl part of the substituents $R^1$ and/or $R^2$ contains up to 10 carbon atoms, preferably up to 9 carbon atoms, more preferably up to 6 carbon atoms, and in which each optionally substituted group independently is substituted by one or more halogen atoms or nitro, cyano, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, halo- or dihalo-phenyl or pyridyl groups. Any alkyl, alkenyl or alkynyl group may be linear or branched. A halogen atom suitably denotes a fluorine, chlorine or bromine atom.

The invention especially relates to compounds of the general formula I, in which $R^1$ represents a hydrogen atom, a $C_{1-10}$ alkyl group, in particular a hydrogen atom or a methyl group.

Another preferred embodiment of the present invention are the compounds of formula I, wherein $R^2$ represents a hydrogen atom or a $C_{1-10}$ alkyl group or a $C_{3-14\ 10}$ alkenyl group. Those compounds of formula I in which at least one of $R^1$ and $R^2$ represents a hydrogen atom are particularly preferred.

Particularly preferred are compounds of formula I, in which the phenyl group

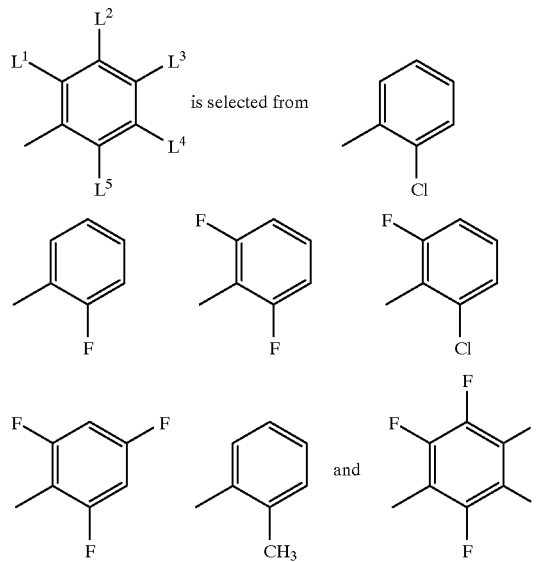

The compounds according to general formula I are oils, gums, or, predominantly crystalline solid materials. They are superior through their valuable fungicidal properties, in particular their enhanced systemicity and enhanced fungicitoxity against rice diseases and powdery mildews. For example, they can be used in agriculture or related fields for the control of phytopathogenic fungi such as *Alternaria solani, Botrytis cinerea, Cercospora beticola, Cladosporium herbarum, Corticium rolfsii, Erysiphe graminis, Helminthosporium tritici repentis, Leptosphaeria nodorum, Micronectriella nivalis, Monilinia fructigena, Mycosphaerella ligulicola, Mycosphaerella pinodes, Pyricularia grisea f.sp. oryzae, Rhizoctonia solani, Venturia inaequalis, Uncinula necator* and *Sclerotinia sclerotiorum*, in particular for the control of *Uncinula necator, Pyricularia grisea f.sp. oryzae* and *Rhizoctonia solani*. The compounds of general formula I according to the invention possess a high fungicidal activity within a wide concentration range and may be used in agriculture without any difficulties.

Moreover, the compounds according to the invention show enhanced residual control of fungi, in particular of grape powdery mildew compared with conventional fungicides.

Good results in terms of control of phythopathogenic fungi are obtained with a compound as defined in formula I wherein:

at least one of $L^1$ and $L^5$ represents a halogen atom; and/or $R^1$ represents hydrogen.

Especially good results in terms of control of phytopathogenic fungi are obtained by using, for example, the following compounds of formula I:

5-chloro-6-(2-chloro-6-fluorophenyl)-7-(2,2,2-trifluoroethylamino)-[1,2,4]triazolo[1,5-a]pyrimidine, 5-chloro-6-(2,6-difluorophenyl)-7-(2,2,2-trifluoroethylamino)-[1,2,4]triazolo[1,5-a]pyrimidine, 5-chloro-7-(2,2,2-tri-fluoroethylamino)-6-(2,4,6-trifluorophenyl)-[1,2,4]triazolo[1,5-a]pyrimidine, 5-chloro-6-(2-chlorophenyl)-7-(2,2,2-trifluoroethylamino)-[1,2,4]triazolo[1,5-a]pyrimidine, 5-chloro-6-(2-fluorophenyl)-7-(2,2,2-trifluoroethylamino)-[1,2,4]triazolo[1,5-a]pyrimidine, 5-chloro-6-(2-chloro-6-fluorophenyl)-7-[2-(1,1,1-trifluoro)propylamino]-[1,2,4]triazolo[1,5-a]pyrimidine, 5-chloro-6-(2,6-difluorophenyl)-7-[2-(1,1,1-trifluoro)propylamino]-[1,2,4]triazolo[1,5-a]pyrimidine, 5-chloro-6-(2,4,6-trifluorophenyl)-7-[2-(1,1,1-trifluoro)propylamino]-[1,2,4]triazolo[1,5-a]pyrimidine, 5-chloro-6-(2-methylphenyl)-7-[2-(1,1,1-trifluoro)propylamino]-[1,2,4]triazolo[1,5-a]pyrimidine, 5-chloro-6-(2-fluorophenyl)-7-[2-(1,1,1-trifluoro)propylamino]-[1,2,4]triazolo[1,5-a]pyrimidine, 5-chloro-6-(2-chlorophenyl)-7-[2-(1,1,1-trifluoro)propylamino]-[1,2,4]triazolo[1,5-a]pyrimidine, 5-chloro-6-(2,4,6-trifluorophenyl)-7-[N-(2,2,2-trifluoroethyl)-N-allylamino]-[1,2,4]triazolo[1,5-a]pyrimidine, 5-chloro-6-(2-chloro-6-fluorophenyl)-7-[N-(2,2,2-trifluoroethyl)-N-allylamino]-[1,2,4]triazolo[1,5-a]pyrimidine, 5-chloro-6-(2-fluorophenyl)-7-[N-(2,2,2-trifluoroethyl)-N-allylamino]-[1,2,4]triazolo[1,5-a]pyrimidine, 5-chloro-6-(2,6-difluorophenyl)-7-[N-(2,2,2-trifluoroethyl)-N-allylamino]-[1,2,4]triazolo[1,5-a]pyrimidine, 5-chloro-6-(2-chlorophenyl)-7-[N-(2,2,2-trifluoroethyl)-N-allylamino]-[1,2,4]triazolo[1,5-a]pyrimidine, 5-chloro-6-(2-methylphenyl)-7-[N-(2,2,2-trifluoroethyl)-N-allylamino]-[1,2,4]triazolo[1,5-a]pyrimidine, 5-chloro-6-(2-fluorophenyl)-7-[N-(2,2,2-trifluoroethyl)-N-ethylamino]-[1,2,4]triazolo[1,5-a]pyrimidine, 5-chloro-6-(2,6-difluorophenyl)-7-[N-(2,2,2-trifluoroethyl)-N-ethylamino]-[1,2,4]triazolo[1,5-a]pyrimidine, 5-chloro-6-(2,4,6-trifluorophenyl)-7-[N-(2,2,2-trifluoroethyl)-N-ethylamino]-[1,2,4]triazolo[1,5-a]pyrimidine, 5-chloro-6-(2-chloro-6-fluorophenyl)-7-[N-(2,2,2-trifluoroethyl)-N-ethylamino]-[1,2,4]triazolo[1,5-a]pyrimidine, 5-chloro-6-(2-chlorophenyl)-7-[N-(2,2,2-trifluoroethyl)-N-ethylamino]-[1,2,4]triazolo[1,5-a]pyrimidine, 5-chloro-6-(2-methylphenyl)-7-[N-(2,2,2-trifluoroethyl)-N-ethylamino]-

[1,2,4]triazolo[1,5-a]pyrimidine, 5-chloro-6-(2-chloro-6-fluorophenyl)-7-[N-(2,2,2-trifluoroethyl)-N-(2-methylpropyl)-amino]-[1,2,4]triazolo[1,5-a]pyrimidine, 5-chloro-6-(2,6-difluorophenyl)-7-[N-(2,2,2-trifluoroethyl)-N-(2-methylpropyl)amino]-[1,2,4]triazolo[1,5-a]pyrimidine, 5-chloro-6-(2-fluorophenyl)-7-[N-(2,2,2-trifluoroethyl)-N-(2-methylpropyl)amino]-[1,2,4]triazolo[1,5-a]pyrimidine, 5-chloro-6-(2,4,6-trifluorophenyl)-7-[N-(2,2,2-trifluoroethyl)-N-(2-methylpropyl)amino]-[1,2,4]triazolo[1,5-a]pyrimidine, 5-chloro-6-(2-methylphenyl)-7-[N-(2,2,2-trifluoroethyl)-N-(2-methylpropyl)amino]-[1,2,4]triazolo[1,5-a]pyrimidine, 5-chloro-6-(2-fluorophenyl)-7-[N-(2,2,2-trifluoroethyl)-N-methylamino]-[1,2,4]triazolo[1,5-a]pyrimidine, 5-chloro-6-(2,6-difluorophenyl)-7-[N-(2,2,2-trifluoroethyl)-N-methylamino]-[1,2,4]triazolo[1,5-a]pyrimidine, 5-chloro-6-(2,4,6-trifluorophenyl)-7-[N-(2,2,2-trifluoroethyl)-N-methylamino]-[1,2,4]triazolo[1,5-a]pyrimidine, 5-chloro-6-(2-methylphenyl)-7-[N-(2,2,2-trifluoroethyl)-N-methylamino]-[1,2,4]triazolo[1,5-a]pyrimidine, 5-chloro-6-(2-fluorophenyl)-7-[N-(2,2,2-trifluoroethyl)-N-isopropylamino]-[1,2,4]triazolo[1,5-a]pyrimidine, 5-chloro-6-(2,6-difluorophenyl)-7-[N-(2,2,2-trifluoroethyl)-N-isopropylamino]-[1,2,4]triazolo[1,5-a]pyrimidine, 5-chloro-6-(2,4,6-trifluorophenyl)-7-[N-(2,2,2-trifluoroethyl)-N-isopropylamino]-[1,2,4]triazolo[1,5-a]pyrimidine, 5-chloro-6-(2-chloro-6-fluorophenyl)-7-[N-(2,2,2-trifluoroethyl)-N-isopropylamino]-[1,2,4]triazolo[1,5-a]pyrimidine, 5-chloro-6-(2,6-difluorophenyl)-7-[N-(2,2,2-trifluoroethyl)-N-(1-phenylethyl)amino]-[1,2,4]triazolo[1,5-a]pyrimidine, 5-chloro-6-(2-fluorophenyl)-7-[N,N-di-(2,2,2-trifluoroethyl)-amino]-[1,2,4]triazolo[1,5-a]pyrimidine, 5-chloro-6-(2-methylphenyl)-7-[N,N-di-(2,2,2-trifluoroethyl)amino]-[1,2,4]triazolo[1,5-a]pyrimidine, 5-chloro-6-(2-chlorophenyl)-7-[N,N-di-(2,2,2-trifluoroethyl)-amino]-[1,2,4]triazolo[1,5-a]pyrimidine, 5-chloro-6-(2-chloro-6-fluorophenyl)-7-[N,N-di-(2,2,2-trifluoroethyl)amino]-[1,2,4]triazolo[1,5-a]pyrimidine, 5-chloro-6-(2,6-difluorophenyl)-7-[N, N-di-(2,2,2-trifluoroethyl)-amino]-[1,2,4]triazolo[1,5-a]pyrimidine, 5-chloro-6-(2,4,6-trifluorophenyl)-7-[N,N-di-(2,2,2-trifluoroethyl)amino]-[1,2,4]triazolo [1,5-a]pyrimidine, 5-chloro6-(2,6-difluorophenyl)-7-[N,-(2,2,2-trifluoroethyl)-N-(1,2-dimethylpropyl)amino]-[1,2,4]triazolo[1,5-a]pyrimidine.

The present invention further provides a process for the preparation of a compound of formula I as defined above which comprises
treating a compound of the general formula II

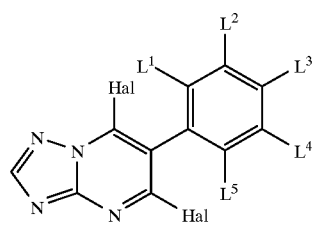

(II)

in which
L¹ through L⁵ and Hal are as defined in any one of the preceding claims; with an amine or amide of the general formula III

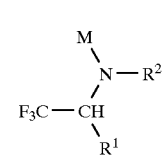

(III)

in which
R¹ and R² are as defined hereinbefore,
M represents a hydrogen atom or a free or complexed metal atom, preferably selected from the group consisting of Li, Na, K, Zn and Cu, to produce a compound of formula I.

Compounds of formula II are known e.g. from EP 0 550 113 and are conventionally prepared by reacting 3-amino-1,2,4-triazole with 2-phenyl-substituted malonic acid ester of formula IV,

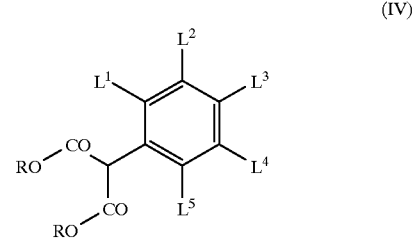

(IV)

wherein R represents alkyl, under alkaline conditions, preferably using high boiling tertiary amines as for example tri-n-butylamine.

The resulting 5,7-dihydroxy-6-phenyltriazolopyrimidines are subsequently treated with a halogenating agent, preferably with a brominating or chlorinating agent, such as phosphorus oxybromide or phosphorus oxychloride, neat or in the presence of a solvent. The reaction is suitably carried out at a temperature in the range from 0° C. to 150° C., the preferred reaction temperature being from 80° C. to 125° C.

The reaction between the 5,7-dihalo-6-phenyltriazolopyrimidines of formula II and the amine or amide of formula III is conveniently carried out in the presence of a solvent. Suitable solvents include ethers, such as dioxane, diethyl ether and, especially, tetrahydrofuran, halogenated hydrocarbons such as dichloromethane and aromatic hydrocarbons, for example toluene. The reaction is suitably carried out at a temperature in the range from 0° C. to 70° C., the preferred reaction temperature being from 10° C. to 35° C. It is also preferred that the reaction is carried out in the presence of a base. Suitable bases include tertiary amines, such as triethylamine, and inorganic bases, such as potassium carbonate or sodium carbonate. Alternatively, an excess of the compound of formula III may serve as a base.

The compounds according to the invention may also be obtained by reacting a 7-amino-5-halo-6-phenyltriazolopyrimidine with a trifluoroalkanoic acid or a reactive derivative thereof, in particular with trifluoroacetic acid anhydride, in the presence of a base and subsequent reduction of the resulting trifluoroalkanoic amide.

The amines of formula III, wherein M represents a hydrogen atom, are well-known in the literature or commercially available or may be prepared analogously to methods that are known per se. The amides of formula III, wherein M represents a metal atom are, as a rule, obtained from the corresponding amines (M=hydrogen) by reaction with an alkyl lithium compound optionally followed by a transmetallation reaction.

The compounds of general formula I have been found to have fungicidal activity. Accordingly, the invention further provides a fungicidal composition which comprises a carrier and, as active ingredient, at least one compound of formula I as defined above. A method of making such a composition is also provided which comprises bringing a compound of formula I as defined above into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally gaseous but which has been compressed to form a liquid, and any of the carriers normally used in formulating fungicidal compositions may be used.

The compositions may be manufactured into e.g. emulsion concentrates, solutions which may be sprayed directly or diluted, diluted emulsions, wettable powders, soluble powders, dusts, granulates, water-dispersible granulates, microencapsulates by well-established procedures. The form of application such as spraying, atomizing, dispersing, pouring may be chosen like the compositions according to the desired objectives and the given circumstances.

The formulations, i.e. the compositions which comprise at least one compound according to general formula I and optionally solid and/or liquid auxiliaries and adjuvants, may be prepared by well-established procedures, e.g. intensive mixing and/or grinding of the active ingredients with other substances, such as fillers, solvents, solid carriers, and optionally surface-active compounds (tensides).

Solvents may be aromatic hydrocarbons, preferably the fractions $C_8$ to $C_{12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, dimethyl sulfoxide, alkyl formamides, epoxidized vegetable oils, e.g. epoxidized coconut or soybean oil, water. Mixtures of different liquids are often suitable.

Solid carriers, which may be used for dusts or dispergible powders, may be mineral fillers, such as calcite, talc, kaolin, montmorillonite, attapulgite. The physical properties may be improved by addition of highly dispersed silica gel or highly dispersed polymers. Carriers for granulates may be porous material, e.g. pumice, broken brick, sepiolite, bentonite, nonsorptive carriers may be calcite or sand. Additionally, a multitude of pregranulated inorganic or organic materials may be used, such as dolomite or crushed plant residues.

Fungicidal compositions are often formulated and transported in concentrated form which is subsequently diluted by the user before application. The presence of small amounts of a carrier which is a surface-active agent facilitates this process of dilution. Thus, preferably one carrier in a composition according to the invention is a surface active agent. For example, the composition may contain at least two carriers, at least one of which is a surface active agent.

Suitable surface-active substances may be non-ionogenic, anionic or cationic tensides with good dispersing, emulgating and wetting properties depending on the nature of the compound according to general formula I to be formulated. Tensides may also mean mixtures of tensides.

Suitable tensides may be so-called water-soluble soaps as well as water-soluble synthetic surface-active compounds.

Soaps usually are alkali, earth alkali or optionally-substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyltaurine salts of fatty acids may be used.

However, so-called synthetic tensides are preferably used, especially fatty sulphonates, fatty sulfates, sulfonated benzimidazole derivatives or alkyl aryl sulphonates.

The fatty sulfates or fatty sulphonates are normally used as alkali, earth alkali or optionally-substituted ammonium salts and have an alkyl moiety of 8 to 22 carbon atoms, whereby alkyl also means the alkyl moiety of acyl residues, such as the sodium or calcium salt of lignin sulfonic acid, of sulfuric acid dodecylate or of a mixture of fatty alcohols prepared from natural fatty acids. This also includes the salts of sulfuric acid esters, sulfonic acids and adducts of fatty alcohols and ethylene oxide. The sulfonated benzimidazole derivatives preferably contain 2 sulfonic acid residues and a fatty acid residue with 8 to 22 carbon atoms. Alkyl aryl sulphonates are, for example, the sodium, calcium or triethyl ammonium salts of dodecyl benzene sulfonic acid, dibutyl naphthalene sulfonic acid or of a condensate of naphthalene sulfonic acid and formaldehyde.

Furthermore, phosphates, such as the salts of the phosphoric acid ester of a p-nonylphenol-(4–14)-ethylene oxide adduct or phospholipids, may be used.

Non-ionic tensides are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols.

Other suitable non-ionic tensides are the water-soluble, 20 to 250 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit.

Examples of non-ionic tensides are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol.

Furthermore, fatty acid esters of polyoxy ethylene sorbitan, such as polyoxy ethylene sorbitan trioleate may be used.

Cationic tensides preferably are quaternary ammonium salts, which have at least one alkyl residue with 8 to 22 carbon atoms and, furthermore, low, optionally-halogenated alkyl, benzyl or hydroxyalkyl residues. The salts are preferably halides, methyl sulfates or alkyl sulfates, e.g. stearyl trimethyl ammonium chloride or benzyl bis(2-chloroethyl) ethyl ammonium bromide.

The compositions of the invention may for example be formulated as wettable powders, dusts, granules, solutions, emulsifiable concentrates emulsions, suspension concentrates and aerosols. Wettable powders usually contain 25%, 50% or 75% w/w of active ingredient and usually contain in addition to solid inert carrier, 3%–10% w/w of a dispersing agent and, where necessary, 0%–10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5%–10% w/w of active ingredient. Granules are usually prepared to have a size between 10 and 100 mesh ASTM (approx. 2.00 mm–0.15 mm), and may be manufactured by agglomeration or impregnation techniques. Generally, granules will contain 0.5%–75% active ingredient and 0–10% w/w of additives such as stabilizer, surfactants, slow release modifiers and binding agents. The so called "dry flowable powders" consist of relatively small granules having a relatively high concentration of active ingredient. Emulsifiable concentrates usually contain, in addition to a solvent or a mixture of solvents, 1%–50% w/v active ingredient, 2%–20% w/v emulsifiers and 0%–20% w/v of other additives such as stabilizers, penetrants and corrosion inhibitors. Suspension concentrates are usually compounded so as to obtain a stable, nonsedimenting flowable product and usually contain 10%–75% w/w active ingredient, 0.5%–15% w/w of dispersing agents, 0.1%–10% w/w of suspending agents such as protective colloids and thixotropic agents, 0%–10% of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide slow release of the fungicidal compounds into the environment of a plant which is to be protected. Such slow-release formulations could, for example, be inserted in the soil adjacent to the roots of a plant, or could include an adhesive component enabling them to be applied directly to the stem of a plant.

As commodity the compositions may preferably be in a concentrated form whereas the end-user generally employs diluted compositions. The compositions may be diluted to a concentration of 0.001% of active ingredient (a.i.). The doses usually are in the range from 0.01 to 10 kg a.i./ha.

The compositions of this invention can comprise also other compounds having biological activity, e.g. compounds having similar or complementary fungicidal activity or compounds having plant growth regulating, herbicidal or insecticidal activity. The other fungicidal compound can be, for example, one which is capable of combating other diseases of cereals (e.g. wheat) such as Septoria, Gibberella and Helminthosporum spp., seed and soil borne diseases and downy and powdery mildews on vines and powdery mildew and scab on apples etc. These mixtures of fungicides can have a broader spectrum of activity than the compound of general formula I alone. Furthermore, the other fungicide can have a synergistic effect on the fungicidal activity of the compound of general formula I.

Examples of the other fungicidal compound are carbendazim, benomyl, thiophanate-methyl, thiabendazole, fuberidazole, etridiazole, dichlofluanid, cymoxanil, oxadixyl, ofurace, metalaxyl, furalaxyl, benalaxyl, fosetyl-aluminium, fenarimol, iprodione, procymidione, vinclozolin, penconazole, myclobutanil, R0151297, S3308, pyrazophos, ethirimol, ditalimfos, tridemorph, triforine, nuarimol, triazbutyl, guazatine, triacetate salt of 1,1'-iminodi (octamethylene)-diguanidine, propiconazole, prochloraz, flutriafol, hexaconazole, flusilazole, triadimefon, triadimenol, diclobutrazol, fenpropimorph, pyrifenox, cyproconazole, tebuconazole, epoxiconazole, 4-chloro-N-(cyano(ethoxy)methyl)benzamide, fenpropidin, chlorozolinate, diniconazol, imazalil, fenfuram, carboxin, oxycarboxin, methfuroxam, dodemorph, blasticidin S, kasugamycin, edifenphos, kitazin P, cycloheximide, phthalide, probenazole, isoprothiolane, tricyclazole, pyroquilon, chlorbenzthiazon, neoasozin, polyoxin D, validamycin A, mepronil, flutolanil, pencycuron, diclomezin, phenazineoxide, nickel dimethyldithiocarbamate, techlofthalam, bitertanol, bupirimate, etaconazole, streptomycin, cypofuram, biloxazol, quinomethionate, dimethirimol, 1-(2-cyano-2-methoxyimino-acetyl)-3-ethyl urea, fenapanil, tolclofosmethyl, pyroxyfur, polyram, maneb, mancozeb, captafol, chlorothalonil, anilazin, thiram, captan, folpet, zineb, propineb, sulfur, dinocap, binapacryl, nitrothalisopropyl, dodine, dithianon, fentin hydroxide, fentin acetate, tecnazene, quintozen, dichloran, copper-containing compounds such as copper oxychloride, copper sulfate and Bordeaux mixture as well as organic mercury compounds, kresoxim-methyl, azoxystrobin, SSF-126, pyrimethanil, cyprodinil, spiroxamine, fludioxonil, quinoxyfen, BION, carpropamid, metconazole, dimethomorph, famoxadone, propanocarb, flumetover, fenpiclonil, fluazinam, mepanipyrim, triazoxide, chlorothalonil.

The compounds of general formula I can be mixed with soil, peat or other rooting media for the protection of the plants against seed-borne, soil-borne or foliar fungal diseases.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit such as apples and peas, peanuts, potatoes, vegetables and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLE 1

5-Chloro-6-(2-chloro-6-fluorophenyl)-7-N-(2,2,2-trifluoroethylamino)-1,2,4-triazolo[1.5a]pyrimidine A mixture of 2,2,2-trifluoroethylamine (1.4 mmoles), triethylamine (1.4 mmoles) and dichloromethane (10 ml) is added to a mixture of 5,7- dichloro-6-(2-chloro-6- fluorophenyl)-1,2,4-triazolo[1.5a]pyrimidine (1.4 mmoles) and dichloromethane (30 ml) under stirring. The reaction mixture is stirred 16 hours at room temperature, subsequently washed two times with 1N hydrochloric acid and once with water. The organic layer is separated, dried with anhydrous sodium sulfate and the solvent is evaporated under reduced pressure. Treatment of the resulting light brown oil with tert-butyl methyl ether (50 ml) yields beige crystals (79% of theory) having a melting point of 194–197° C.

EXAMPLES 2–45

The following examples (Table I; structure and melting point) are synthesized analogously to Example 1.

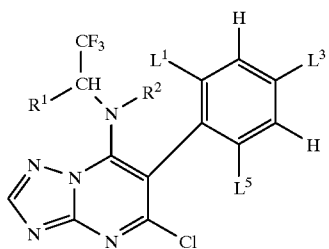

| Example | $R^1$ | $R^2$ | $L^1$ | $L^3$ | $L^5$ | melting point (° C.) |
|---|---|---|---|---|---|---|
| 2  | H   | H           | Cl  | H | H | 165 |
| 3  | H   | H           | F   | F | F | 195 |
| 4  | H   | H           | F   | H | H | 180 |
| 5  | H   | H           | F   | H | F | 137 |
| 6  | CH₃ | H           | Cl  | H | F | 165–176 |
| 7  | CH₃ | H           | F   | H | F | 166–167 |
| 8  | CH₃ | H           | F   | F | F | 184–185 |
| 9  | CH₃ | H           | CH₃ | H | H | 149–151 |
| 10 | CH₃ | H           | F   | H | H | 128–130 |
| 11 | CH₃ | H           | Cl  | H | H | 129–130 |
| 12 | H   | allyl       | F   | F | F | 104–105 |
| 13 | H   | allyl       | Cl  | H | F | 145–146 |
| 14 | H   | allyl       | F   | H | H | 128 |
| 15 | H   | allyl       | F   | H | F | 109–111 |
| 16 | H   | allyl       | Cl  | H | H | 129–130 |
| 17 | H   | allyl       | CH₃ | H | H | 123–130 |
| 18 | H   | ethyl       | F   | H | H | 136–139 |
| 19 | H   | ethyl       | F   | H | F | 164–166 |
| 20 | H   | ethyl       | F   | F | F | 133–134 |
| 21 | H   | ethyl       | Cl  | H | F | 199–202 |
| 22 | H   | ethyl       | Cl  | H | H | 150–158 |
| 23 | H   | ethyl       | CH₃ | H | H | 174–178 |
| 24 | H   | 2-methylpropyl | Cl | H | F | 175 |
| 25 | H   | 2-methylpropyl | F  | H | F | 154–155 |

| Example | $R^1$ | $R^2$ | $L^1$ | $L^3$ | $L^5$ | melting point (° C.) |
|---|---|---|---|---|---|---|
| 26 | H | 2-methylpropyl | F | H | H | 144 |
| 27 | H | 2-methylpropyl | F | F | F | 133–134 |
| 28 | H | 2-methylpropyl | CH₃ | H | H | 154–155 |
| 29 | H | methyl | F | H | H | 142–143 |
| 30 | H | methyl | F | H | F | 175–177 |
| 31 | H | methyl | F | F | F | 163 |
| 32 | H | methyl | F | H | Cl | 178–180 |
| 33 | H | methyl | CH₃ | H | H | 147–149 |
| 34 | H | isopropyl | F | H | F | 147–150 |
| 35 | H | isopropyl | F | H | Cl | 178–183 |
| 36 | H | isopropyl | F | F | F | 154–158 |
| 37 | H | isopropyl | F | H | H | 167–170 |
| 38 | H | 1-phenylethyl | F | H | H | oil |
| 39 | H | 2,2,2-trifluoroethyl | Cl | H | H | 212–213 |
| 40 | H | 2,2,2-trifluoroethyl | CH₃ | H | H | 223–226 |
| 41 | H | 2,2,2-trifluoroethyl | F | H | H | 185–186 |
| 42 | H | 2,2,2-trifluoroethyl | F | H | Cl | 234–237 |
| 43 | H | 2,2,2-trifluoroethyl | F | H | F | 208–210 |
| 44 | H | 2,2,2-trifluoroethyl | F | F | F | 177–179 |
| 45 | H | 1,2-dimethylpropyl | F | H | F | 154–158 |

Biological Investigations

A. Determination of Minimum Inhibitory Concentration by Test Compounds in the Serial Dilution Test with Various Phytopathogenic Fungi The MIC (Minimum Inhibitory Concentration) value, which indicates the lowest concentration of the active ingredient in the growth medium which causes a total inhibition of myecelial growth, is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 mg/ml. For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min.

The respective inocula (*Altemara solani*, ALTESO; *Botrytis cinerea*, OTRCI; *Leptosphaeda nodorum*, LEPTNO; *Phytophthora infestans*, PHYTIN; *Magnaporthe grisea f. sp. oryzae*, PYRIOR; *Pyrenophora teres*, PYRNTE; *Rhizoctonia solani*, RHIZSO;) are added into the wells as spore suspensions (50 ml; $5 \times 10^5$/ml) or agar slices (6 mm) of an agar culture of the fungus.

After 6–12 days incubation at suitable temperatures (18–25° C.), the MIC values are determined by visual inspection of the plates (Table II; n. t.=not tested).

TABLE II

| Ex. No. | ALTESO | BOTRCI | LEPTNO | PHYTIN | PYRIOR | PYRNTE | RHISZO |
|---|---|---|---|---|---|---|---|
| 1  | 3.13  | 1.56  | 6.25 | 12.5 | 0.78 | 6.25 | 6.25 |
| 2  | 12.5  | 6.25  | 50   | 12.5 | 0.78 | 12.5 | 25 |
| 3  | 1.56  | 1.56  | 6.25 | 25   | 0.2  | 6.25 | 6.25 |
| 6  | 3.13  | 12.5  | 25   | 110  | 3.13 | 25   | 6.25 |
| 7  | 1.56  | 25    | 50   | 110  | 0.78 | 12.5 | 6.25 |
| 8  | 0.78  | 3.13  | 3.13 | 110  | 0.78 | 6.25 | 3.13 |
| 9  | 25    | 25    | 12.5 | 110  | 3.13 | 110  | 12.5 |
| 10 | 6.25  | 110   | 50   | 25   | 1.56 | 110  | 12.5 |
| 11 | 3.13  | 6.25  | 25   | 100  | 0.39 | 6.25 | 6.25 |
| 12 | 0.39  | 0.78  | 3.13 | 110  | 0.04 | 3.13 | 0.78 |
| 13 | 3.13  | 3.13  | 110  | 110  | 0.1  | 110  | 1.56 |

TABLE II-continued

| Ex. No. | ALTESO | BOTRCI | LEPTNO | PHYTIN | PYRIOR | PYRNTE | RHISZO |
|---|---|---|---|---|---|---|---|
| 15 | 1.56 | 1.56 | 6.25 | 110 | 0.04 | 6.25 | 1.56 |
| 16 | 1.56 | 6.25 | 12.5 | 110 | 0.39 | 50 | 50 |
| 19 | 0.78 | 1.56 | 110 | 110 | 0.04 | 110 | 0.78 |
| 20 | 0.78 | 0.78 | 3.13 | 110 | 0.04 | 1.56 | 0.78 |
| 27 | 0.2 | 0.2 | 0.39 | 110 | 0.04 | 110 | 3.13 |
| 30 | 3.13 | 12.5 | 110 | 110 | 0.78 | 25 | 110 |
| 31 | 0.78 | 3.13 | 50 | 110 | 0.1 | 12.5 | 1.56 |
| standard* | 12.5 | 12.5 | 100 | 110 | 50 | 50 | 100 |

*The following compound has been used as standard:

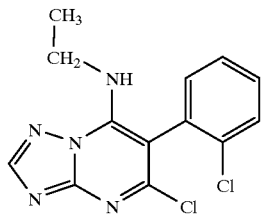

This compound corresponds to the compound of example 2, in which the 7-(2,2,2-trifluoroethyl)amino group has been replaced by an ordinary 7-ethylamino group.

B. Determination of residual control of grape powdery mildew on vine leaves

Method for Evaluation of the compounds of formula I to control mildew on grapes (*Uncinula necator*)

Test plants

Cuttings of cultivar Müller-Thurgau were grown in the greenhose at temperatures between 18° C. and 25° C. and 50 to 70% relative humidity. When 6 to 8 leaves had developed the plants were cut back to 3–4 equally sized leaves. Plants were cultivated in pots containing FLORAGAD as a substrate.

Application

Three to four plants per treatment were used. Application of the compounds of formula I was carried out 3 days before infection in the prophylactic tests. The test plants were sprayed to run off in a spray cabinet using 20 ml of spray wash. The compounds of formula I were dissolved in acetone at a concentration of 0.5%. The stock solution was diluted with water to give the final concentrations. Formulated fungicides were also diluted with water prior to application.

Infection

The plants were artificially infected with conidia of *Uncinula necator* by dusting spores from freshly sporulating grape leaves from the *Uncinula necator* stock culture over the test plants. The spores were allowed to settle on the leaves for 1 hour. The plants remained in the greenhouse without additional light at temperatures between 16° C. and 30° C. for 24 hours.

Evaluation

Evaluation was carried out 21 days after infection by assessing the percentage of infected leaf area of each of the 4 treated leaves. The activity in % was calculated using the ABBOTT formula:

$$\% \text{ activity} = 100 - \frac{\% \text{ infection in treated}}{\% \text{ infection in untreated}} \times 100$$

The results of this evaluation are shown in Table III:

TABLE III

| | Uncinula necator on Vines | |
|---|---|---|
| Example No. | Rate (ppm a.i.) | Efficacy (%) |
| 3 | 25 | 100 |
| | 12.5 | 100 |
| | 6.25 | 100 |
| | 3.13 | 91 |
| 2 | 25 | 38 |
| | 12.5 | 19 |
| | 6.25 | 5 |
| | 3.13 | 0 |
| 8 | 25 | 100 |
| | 12.5 | 100 |
| | 6.25 | 100 |
| | 3.13 | 97 |
| standard* | 25 | 5 |
| | 12.5 | 11 |
| | 6.25 | 2 |
| | 3.13 | 0 |

*The same compound as in the investigations regarding the MIC values has been used as standard.

C. Foliar Systemicity

C-1: Grape variety Müller-Thurgau
PATHOGEN: *Uncinula necator*
TEST PROCEDURE:

1. Grape cuttings are grown in 8 cm diameter plastic in the greenhouse.

2. Formulated compounds are applied to a young fully expanded leaf in a transverse band using an airbrush with a 0.5 mm circular nozzle at an air pressure of 500 mbar. The band is sprayed onto the lower leaf surface, perpendicular to the leaf axis using a cardboard mask with a 5-mm wide slit. The location of the band is marked on the upper leaf surface using a permanent marker and is typically 4 cm from the leaf apex. After application, the plants are not moved until the bands are dry.

3. After treated plants have dried, they are moved to the greenhouse and kept there for 2 days to allow for movement of the compounds. The plants are maintained with bottom watering.

4. Two days after application, the grape plants are inoculated by dusting them with powdery mildew conidia in the greenhouse. Sporulating diseased leaves from stock culture plants are brushed with a brush in the air over the test plants so that the conidia can settle onto the upper leaf surfaces of the test plants. Evaluations are made 12–14 days after inoculation.

C-2 Wheat Powdery Mildew (WPM):
HOST: Wheat (*Triticum aestivum* L.) variety Kanzler
PATHOGEN: *Erysighe graminis* DC. f.sp. *tritici* E. Marchal TEST PROCEDURE:
1. Wheat seed (8/pot) is planted in 8 cm diameter plastic pots in the greenhouse.
2. When the primary leaf is fully expanded, the plants are cut back to four in each pot of which two are marked with a permanent marker 5 cm below the leaf tip on the upper leaf surface. Thus there are two band-treated and two untreated plants in each pot.
3. A pipette is used to apply 5 μl of the formulated compound in a band on the lower leaf surface opposite the mark. The application band should cover the whole leaf width. After application, the plants are not moved until the bands are dry (half an hour or so later).
4. After treated plants have dried, they are moved to the greenhouse and kept there for 2 days to allow for movement of the compounds. The plants are maintained with bottom watering.
5. Two days after application, the plants are inoculated by dusting them with powdery mildew conidia in the greenhouse. Evaluations are made 7–8 days after inoculation. Alternatively, plants are inoculated with *Puccinia recondita* (wheat leaf rust pathogen) and evaluations made 7–8 days thereafter.

Evaluation

Three types of compound movement are assessed by evaluating disease in three areas of each band-treated leaf.

Translaminar movement: The percent disease area is assessed for the translaminar band area (marked area of the upper leaf surface directly opposite where band was applied on the lower leaf surface; width of band approximately 5 mm). Translaminar disease control is then calculated using the following formula:

$$\% \text{ disease control} = 100 - \frac{\% \text{ disease in treated plants}}{\% \text{ disease in untreated plants}} \times 100$$

Distal movement and proximal movement: The distal and proximal disease-free zones on the upper leaf surface are measured in mm. The distal direction is from the band toward the leaf apex and the proximal direction is from the band toward the leaf base. The percent of the disease-free zone relative to the entire distance between the band and leaf apex or base is calculated (for Grape 40 mm equals 100%). If disease is noticeably lighter in the distal or proximal area this is also noted.

FORMULATION AND CONTROLS:
1. The compounds are formulated in a solvent/surfactant system consisting of 5% acetone and 0.05% Tween 20 in deionized water.
Compounds are dissolved in acetone prior to dilution with Tween water. Formulated compounds are prepared using deionized water. Compounds are typically tested at 400 ppm
2. Three kinds of controls are included:
Plants band-treated with the solvent surfactant solution and inoculated (Solvent Blank).
Untreated plants which are inoculated (Inoculated Control).
The results of this evaluation are shown in Table IV, in which the diseases have been abbreviated as follows:

| Wheat powdery mildew | WPM |
| Grape powdery mildew | GPM |
| Wheat leaf rust | WLR |

TABLE IV

Foliar Systemicity

| Ex. No. | Disease | Proximal Movement (mm from band) | Distal Movement (mm from band) | Translaminar Activity (%) |
| --- | --- | --- | --- | --- |
| 1 | WPM | 3 | 43 | 100 |
|   | GPM | 6 | 50 | 100 |
|   | WLR | 5 | 48 | 100 |
| 2 | GPM | 8 | 36 | 100 |
|   | WLR | 4 | 21 | 100 |
| 3 | GPM | 7 | 50 | 100 |
|   | WLR | 4 | 23 | 100 |
| 4 | GPM | 7 | 32 | 100 |
|   | WLR | 3 | 6 | 100 |
| Standard[2] | GPM | 2 | 6 | 100 |
|   | WLR | 4 | 8 | 100 |

[2]The following compound has been used as standard:

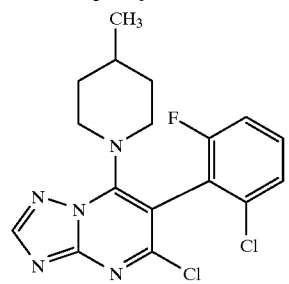

What is claimed is:

1. A compound of formula I

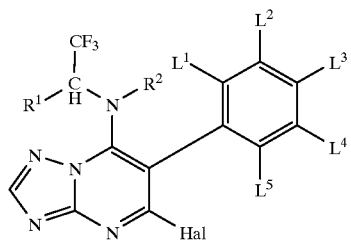
(I)

in which

R¹ represents a hydrogen atom or a methyl group;
R² represents a hydrogen atom or a $C_{1-10}$ alkyl or a $C_{3-10}$ alkenyl group;
Hal represents a bromine or chlorine atom; and
L¹ through L⁵ each independently represent an hydrogen or halogen atom, provided that at least one of L¹ through L⁵ represents a halogen atom.

2. A compound according to claim 1 in which R² represents a hydrogen or a $C_{1-10}$ alkyl group.

3. A compound according to claim 1 in which at least one of R¹ and R² represents a hydrogen atom.

4. A compound according to claim 1 comprising:
5-chloro-6-(2-chloro-6-fluorophenyl)-7-(2,2,2-trifluoroethylamino)-[1,2,4]triazolo[1,5-a]pyrimidine
5-chloro-6-(2,6-difluorophenyl)-7-(2,2,2-trifluoroethylamino)-[1,2,4]triazolo[1,5-a]pyrimidine
5-chloro-7-(2,2,2-trifluoroethylamino)-6-(2,4,6-trifluorophenyl)-[1,2,4]triazolo[1,5-a]pyrimidine
5-chloro-6-(2-chlorophenyl)-7-(2,2,2-trifluoroethylamino)-[1,2,4]triazolo[1,5-a]pyrimidine
5-chloro-6-(2-fluorophenyl)-7-(2,2,2-trifluoroethylamino)-[1,2,4]triazolo[1,5-a]pyrimidine
5-chloro-6-(2-chloro-6-fluorophenyl)-7-[2-(1,1,1-trifluoro)propylamino]-[1,2,4]triazolo[1,5-a]pyrimidine
5-chloro-6-(2,6-difluorophenyl)-7-[2-(1,1,1-trifluoro)propylamino]-[1,2,4]triazolo[1,5-a]pyrimidine
5-chloro-6-(2,4,6-trifluorophenyl)-7-[2-(1,1,1-trifluoro)propylamino]-[1,2,4]triazolo[1,5-a]pyrimidine
5-chloro-6-(2-fluorophenyl)-7-[2-(1,1,1-trifluoro)propylamino]-[1,2,4]triazolo[1,5-a]pyrimidine
5-chloro-6-(2-chlorophenyl)-7-[2-(1,1,1-trifluoro)propylamino]-[1,2,4]triazolo[1,5-a]pyrimidine.

5. A fungicidal composition which comprises a carrier, and as active agent, at least one compound of formula I as defined in claim 1.

6. A method of combating fungus at a locus which comprises treating the locus with a compound of formula I as defined in claim 1.

7. A compound according to claim 1 wherein the phenyl group

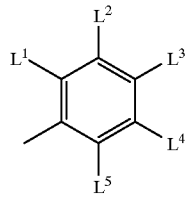

is selected from the group consisting of

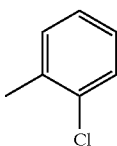 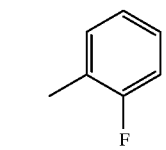 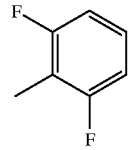

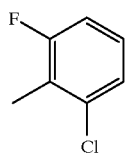 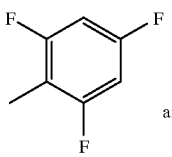 and 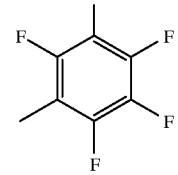

8. A compound according to claim 1 wherein R² is hydrogen; Hal is chlorine; and the phenyl group

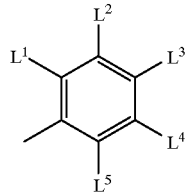

is selected from the group consisting of

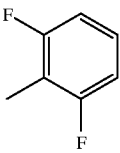 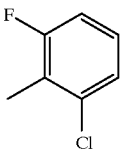 and 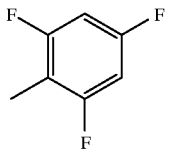

* * * * *